United States Patent [19]

Krauter

[11] Patent Number: 4,706,655
[45] Date of Patent: Nov. 17, 1987

[54] SHIELD FOR ENDOSCOPE ELEVATOR CABLE SEAL

[75] Inventor: Allan I. Krauter, Syracuse, N.Y.
[73] Assignee: Welch Allyn, Inc., Skaneateles Falls, N.Y.
[21] Appl. No.: 900,460
[22] Filed: Aug. 26, 1986
[51] Int. Cl.[4] .............................................. A61B 1/00
[52] U.S. Cl. ........................................................ 128/4
[58] Field of Search .................................. 128/4, 6, 5, 7

[56] References Cited

U.S. PATENT DOCUMENTS

| | | | |
|---|---|---|---|
| 3,561,432 | 2/1971 | Yamaki et al. | 128/6 |
| 4,150,353 | 4/1979 | Huber et al. | 337/231 |
| 4,190,041 | 2/1980 | Chikama | 128/4 |
| 4,198,959 | 4/1980 | Otari | 128/5 |
| 4,407,273 | 10/1983 | Ouchi | 128/6 |
| 4,491,865 | 1/1985 | Danna et al. | 358/98 |
| 4,589,403 | 5/1986 | Ouchi et al. | 128/4 |
| 4,593,680 | 6/1986 | Kubokawa | 128/4 |

FOREIGN PATENT DOCUMENTS 2817922  10/1978  Fed. Rep. of Germany .......... 128/4

Primary Examiner—William H. Grieb
Attorney, Agent, or Firm—Bruns and Wall

[57] ABSTRACT

The control cable for a rockable forceps elevator of a side-looking endoscope has an elastomeric sleeve covering the exterior part of the cable from the endoscope head to the connection of the cable with the elevator. Seals are effected between the sleeve and the wall and between the sleeve and the distal end of the cable. An elongated shield is spaced from the control cable and extends proximally and parallel to the cable, to deflect the forceps or other flexible instrument emerging from the endoscope, and to protect the sleeve and cable from contact with the forceps.

6 Claims, 4 Drawing Figures

SHIELD FOR ENDOSCOPE ELEVATOR CABLE SEAL

BACKGROUND OF THE INVENTION

This invention generally relates to an endoscope or borescope, and is more particularly directed to a side-looking type of endoscope that is inserted into a body cavity and directs an elongated forceps or other medical instrument laterally from the distal end of the endoscope into the body cavity.

Endoscopes of this type employ a so-called elevator, which is a pivotally mounted block that is rocked, by means of a control cable, to divert the endoscope forceps from its axial orientation to a lateral orientation as it exits the head. Conventional endoscopes of this type do not have a sealed elevator cable, however. Instead, such endoscopes employ a metal-wrapped plastic tube that runs the full length of the endoscope insertion tube. The elevator control cable lies within this plastic tube. Body fluids and other fluids are allowed to enter this tube from the head. Then, after use, the tube is flushed from the control end of the insertion tube to wash out the control cable. This rather elaborate and labor intensive procedure complicates the endoscopic procedure considerably, and adds to the patient's expense.

Recently, as described in my earlier, and commonly assigned U.S. patent application No. 830,087 filed Feb. 18, 1986, now abandoned, this problem was addressed by encapsulating the end of the control cable connected to the elevator to seal the cable, and making the elevator more or less open so as to be easily flushable. However, in this type of device there is a need to guide the forceps or other tool so that the same does not touch the encapsulation of the cable thus to prevent abrasion or other damage.

OBJECTS AND SUMMARY OF THE INVENTION

It is an object of the present invention to provide an endoscope which avoids the prior art problems with respect to elevator control cables.

It is a more particular object of this invention to provide such an endoscope which is simple to clean, and which guides the forceps or other instrument away from contact with the elevator cable.

According to an embodiment of this invention, the elevator control cable is sealed at the endoscope head. This is accomplished by encapsulating the elevator control cable in an elastomeric tubular sheath between a stationary part of the head and the moveable forceps elevator. This tubular sleeve compresses in the axial direction as the cable is pulled through the head. A seal is provided at the head, i.e., at the proximal end of the sheath. At the elevator end, i.e., distal end, another seal is effected.

Above the distal end of the cable, an elongated shield projects from the connector that attaches the cable to the elevator. This shield extends proximally and stops the forceps or other instrument from deflecting into the elevator control cable. The shield also assists the emerging forceps or other instrument in remaining oriented in the proper, generally sideways, direction.

The structure of this invention is particularly applicable to endoscopic retrograde cholangiopancreatography or ERCP endoscopes. These endoscopes are inserted into the small intestine through the mouth for visual inspection of the papilla of Vater, especially of the bile duct and pancreatic duct that empty into the small intestine. A fluoroscopic dye is injected through the endoscope so that the examining physician can look for abnormalities, such as gall stones, which can be removed through the bile duct using a thermal type instrument. Also, a drainage tube can be implanted, using the endoscope, into the papilla of Vater.

The present invention is particularly useful in this situation in preventing contamination of the endoscope from the associated body fluids, which can include infected bile or pancreatic fluids.

The above and many other objects, features, and advantages of this invention will be more fully understood from the ensuing detailed description of a preferred embodiment which should be considered in connection with the accompanying drawing.

DETAILED DESCRIPTION OF A PREFERRED EMBODIMENT

Figure 1:
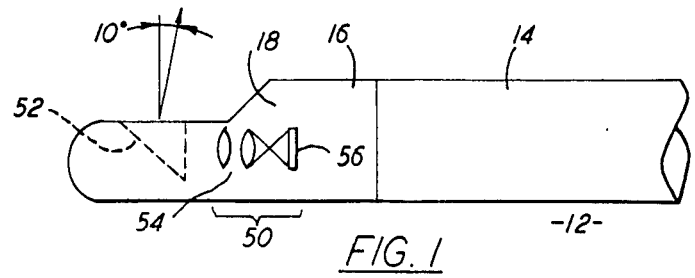
FIG. 1 is a side elevation view of video endoscope apparatus embodying the principles of this invention.
Figure 2:
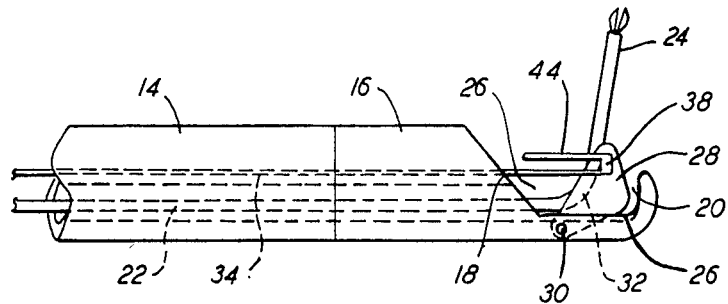
FIG. 2 is another side elevation, partly in ghost, of the head of the endoscopic apparatus of the preferred embodiment.

With reference initially to drawing FIGS. 1 and 2, video endoscopic apparatus of the ERCP type includes a video endoscope 12 formed of an elongated, flexible insertion tube 14 with an endoscope head 16 at the tip or distal end of the insertion tube 14.

Figure 3:
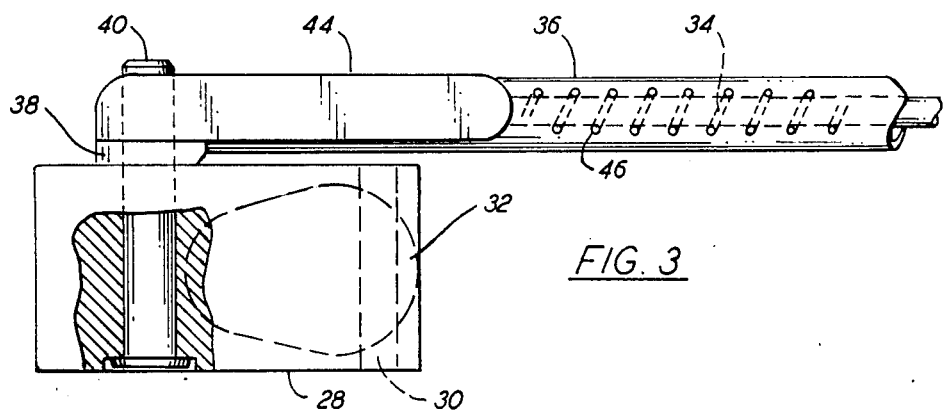
FIG. 3 is a plan view, taken along the lines III-III of FIG. 2, illustrating principal parts of the elevator mechanism.
Figure 4:
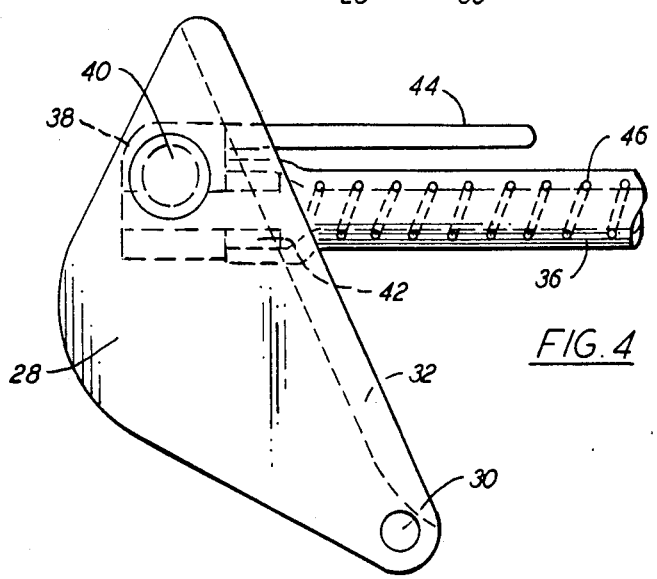
FIG. 4 is a side elevation of the elevator mechanism as shown in FIG. 2.

The endoscope head 16 is of the side-looking type, which views the patient's body cavity laterally, i.e., radially of the insertion tube 14. The head 16 is capable of inserting an endoscopic forceps or other elongated flexible instrument laterally and in the viewing direction. The head 16 and its significant parts are illustrated in FIGS. 3 and 4.

The head 16 is comprised of a shell or housing 18 with a cutout 20 at its right-hand side, that is, the half of the head 16 as illustrated in FIG. 2. A biopsy channel 22 extends through the insertion tube 14 and passes also through the head shell 18 and guides a biopsy forceps 24 or other elongated flexible instrument into the patient's body cavity. A recess 26 in the cutout 20 contains a prism-shaped elevator 28, the same being mounted on a pivot member 30 for rocking motion, i.e., generally clockwise and counter-clockwise as shown in FIG. 2. The elevator 28 has a rounded pocket 32 on its upper surface to divert the forceps 24 away from the endoscope axis.

A control cable or wire 34, preferably of a biocompatible metal such as stainless steel, is connected to the elevator 28 at a point spaced somewhat from the pivot 30, and is manipulated to move the elevator 28. The distal end portion of the control cable 34 is sheathed in a sleeve 36 of elastomeric tubing. The control cable 34 passes through an opening in a fixed wall of the shell 18 of the endoscope head 16, and the proximal end of the sleeve 36 is sealed to the wall by means of a tubing nipple or the like disposed over the cable 34. The inside diameter of this nipple should be somewhat larger than the diameter of the cable 34 so that the cable can pass freely through the nipple. An epoxy sealant or an elastomeric sealant can be used to seal the junction of the nipple and the opening.

The distal end of the control cable 34 is secured to a pivot block 38, the latter being rotatably mounted on the elevator 28 by means of a pivot pin 40. The block 38 has a tubular member 42 that fits within the distal end of the sleeve 36 and is sealed thereto by an epoxy or elastomeric sealant.

Mounted on block 38 above the tubular member 42 and spaced somewhat above the cable 34 (i.e. in the direction that the forceps 24 emerges) there is a spear-shaped elongated shield member 44 that extends proximally and generally parallel to the cable 34. This shield member 44 guides the forceps 24, and protects the sleeve 36 and the cable 34 from abrasion as the forceps 24 moves past.

The shield member 44 extends proximally from the pivot block 38 beyond the proximal extent of the rounded pocket 32 of the elevator 28. In a favorable embodiment, this assembly including the pivot block 38 and the shield member 44 is formed of stainless steel, the shield member 44 having a width (FIG. 3) of about 0.040 inches and a height (FIG. 4) of about 0.025 inches. The center of the shield member 42 is offset outwards a few mils from the center of the cable 34, as seen in FIG. 3.

With the arrangement here shown, if the emerging forceps 24 becomes skewed at an angle outwards (i.e., over the cable 34), the shield member 44 deflects it back into the elevator pocket 32. This shield member 44 can be above the cable 34, as shown in FIG. 3, or to the endoscope axis side of the cable 34. The arrangement keeps the cable 34 or the cable sleeve 36 from contacting the forceps 24. Also, as shown in FIG. 4, an open space is provided between the shield member 44 and the cable sleeve 36 to facilitate flushing of the endoscope head 16 and cleaning of the components after use.

A fine wire coil spring 46 is situated within the sleeve 36 over the cable 34, and is constrained between the wall of the shell 18 and the tubular member 42. This coil spring 46 expands or compresses with the elastic material of the sleeve 36, so that there is substantially no relative movement between the spring 46 and the sleeve 36. This prevents abrasion of the sleeve 36 due to cable movement, and further prevents collapse of the sleeve 36 against the cable 34.

To complete the disclosure, FIG. 1 shows a side-looking optic system 50 employed with the endoscope of this invention. Here, contained within the head 16 the optic system 50 has a reflecting prism 52 followed proximally by focusing lenses 54 and an electronic imager 56. This imager can be, for example, of the type disclosed in U.S. Pat. No. 4,491,865 of Jan. 1, 1985. Transmission lines pass from the imager 56 proximally back through the insertion tube. The reflecting prism has a viewing angle somewhat retrograde, i.e. about ten degrees proximally of true sideways.

The forceps 24 is inserted through the biopsy channel 22 out into the recess and against the pocket 32 of the elevator 28. The control cable 34 is manipulated to rock the elevator 28 up and down as the forceps 24 is inserted. The combined rocking of the elevator 28 and the gradual insertion of the forceps 24 or other elongated flexible instrument diverts the latter into the direction of viewing of the optics 50.

Because the structure of the head 16 leaves the cutout 20 with the recess 26, the elevator 28, and the external part of the cable 34 exposed, the sleeve 36 can be easily cleansed after an endoscopy procedure.

In the preferred embodiment, the elastomeric sleeve is formed of a silicon elastomer, preferably having a low durometer of about 50 Shore A. The sealing material can be of an adhesive elastomer, such as the type sold under the trademark Chemlok.

While a preferred embodiment has been described in detail hereinabove, it should be understood that the invention is not limited to that embodiment, and that many modifications and variations thereof would present themselves to those skilled in the art without departure from the scope and spirit of this invention as defined in the appended claims.

I claim:

1. In an endoscope of the type employed for examination of a patient's body cavity, comprising a flexible tubular member, a viewing head at the distal end of said tubular member, including imaging means in said head for viewing to the side of said head, a biopsy channel within said tubular member and extending to the distal end thereof and exiting through said head, in which channel an elongated flexible instrument can be inserted to pass through said head into the body cavity, an elevator block rotatably mounted on said head for diverting said flexible instrument emerging from said channel to the side of said head generally in the viewing direction of said imaging means, a control cable for said elevator block extending through said flexible tubular member and through a wall of said head for selectively pivoting the elevator block, and pivot means rotatably mounted on said block and affixed into the distal end of said control cable; the improvement further including an elongated shield mounted on said pivot means and spaced from said control cable in the direction of emergence of said flexible instrument, and extending proximally and generally parallel to said cable.

2. The endoscope of claim 1 wherein said pivot means includes a pivot block pivotably mounted on said elevator block and having means affixing said pivot block onto the distal end of said control cable, with said elongated shield being mounted on said pivot block.

3. The endoscope of claim 2, wherein said pivot means includes a pivot pin mounting said pivot block to said elevator block.

4. The endoscope of claim 1, wherein said shield is offset from directly above said cable a fraction of the width of the cable, the offset being in the lateral direction out from said elevator block.

5. The endoscope of claim 1, in which said control cable has a flexible tubular sleeve seal enclosing the distal end of the cable, and said pivot block includes a tubular member receiving the distal end of the cable and sealing against the inner surface of said flexible tubular sleeve seal.

6. The endoscope of claim 1, wherein said elevator block has a rounded pocket on an upper surface thereof to direct said flexible instrument away from the axis of the endoscope, and said elongated shield extends proximally beyond the proximal edge of the rounded pocket.

* * * * *